(12) United States Patent
Roberts et al.

(10) Patent No.: US 11,157,595 B1
(45) Date of Patent: Oct. 26, 2021

(54) TECHNOLOGY ENABLED COMMUNICATIONS PATHWAY BETWEEN HEALTH CARE PROVIDERS AND PATIENTS

(71) Applicant: West Corporation, Omaha, NE (US)

(72) Inventors: Colin Roberts, Blair, NE (US); Pamela A. Mortenson, Blair, NE (US); Fonda J. Narke, Papillion, NE (US); Hendryanto Rilantono, Omaha, NE (US)

(73) Assignee: INTRADO CORPORATION, Omaha, NE (US)

( * ) Notice: Subject to any disclaimer, the term of this patent is extended or adjusted under 35 U.S.C. 154(b) by 984 days.

(21) Appl. No.: 15/053,043

(22) Filed: Feb. 25, 2016

(51) Int. Cl.
  *G06Q 50/18* (2012.01)
  *G06F 19/00* (2018.01)
  *G16H 40/63* (2018.01)
  *G16H 10/60* (2018.01)

(52) U.S. Cl.
  CPC ......... *G06F 19/3418* (2013.01); *G16H 10/60* (2018.01); *G16H 40/63* (2018.01)

(58) Field of Classification Search
  CPC .. G06F 19/00; G06F 19/3418; G06F 19/3456; G06F 19/3481; G06F 19/3462; G06F 21/6245; G06F 19/325; G06F 21/35; G06F 16/27; G16H 10/60; G16H 50/30; G16H 20/30; G16H 20/10; G16H 40/67; G16H 10/20; G16H 40/20; G16H 50/20; G16H 40/63; G16H 50/70; G06Q 50/02; G06Q 50/24; G06Q 10/1095; G06Q 10/1093; G06K 9/00335; G06K 9/00718; G06T 2207/30004; G06T 2207/30196; G06T 7/0012

See application file for complete search history.

(56) References Cited

U.S. PATENT DOCUMENTS

| | | | |
|---|---|---|---|
| 2011/0082711 A1* | 4/2011 | Poeze ................ | A61B 5/14532 705/3 |
| 2014/0088393 A1* | 3/2014 | Bernstein ............ | G06F 19/3456 600/365 |
| 2015/0213225 A1* | 7/2015 | Amarasingham ....... | G06F 19/00 705/2 |

* cited by examiner

*Primary Examiner* — Maroun P Kanaan

(57) ABSTRACT

Providing a technology enabled communications pathway between health care providers and patients, comprising: receiving a bio-metric telemetry data set from a patient, receiving a medication adherence data set from the patient, notifying a health care provider system of at least one potential alarm based on the bio-metric telemetry data set and the medication adherence data set, notifying the patient utilizing positive feedback of the bio-metric telemetry data set and the medication adherence data set, wherein the positive feedback is an affirming communication from the health care provider system indicating that the medication adherence has a positive feedback result in the bio-metric telemetry, notifying the patient of a health care appointment and indicating the positive feedback result the medication adherence has had in the bio-metric telemetry and providing the health care provider system a summary of bio-metric telemetry data set, medication adherence data set and positive feedback prior to the health care appointment.

20 Claims, 20 Drawing Sheets

TECHNOLOGY ENABLED COMMUNICATIONS PATHWAY BETWEEN HEALTH CARE PROVIDERS AND PATIENTS

BACKGROUND

The present disclosure is generally related to customizing communication between health care providers and the patients under their care.

Patients have a multiplicity of technical levels of sophistication; tailoring communications to their sophistication level increases the efficiency and efficacy of the communication. A technological one size fits all approach where one method of communication is used to the exclusion of other forms of communication will only be maximally effective with one target group while leaving other groups at a technological disadvantage.

Therefore, tailoring communication channels to individual patients is sought so that regardless of the level of technological sophistication of the system utilized, the pertinent information is communicated in such a way that the patient understands what is being said and is not put off by the means by which it is communicated.

SUMMARY

In one embodiment, a method comprises at least one of: receiving by at least one processor and at least one memory a bio-metric telemetry data set from a patient, receiving by the at least one processor and the at least one memory a medication adherence data set from the patient, notifying by the at least one processor and the at least one memory a health care provider system of at least one potential alarm based on the bio-metric telemetry data set and the medication adherence data set, notifying by the at least one processor and the at least one memory the patient utilizing positive feedback of the bio-metric telemetry data set and the medication adherence data set, wherein the positive feedback is an affirming communication from the health care provider system indicating that the medication adherence has a positive feedback result in the bio-metric telemetry, notifying by the at least one processor and the at least one memory the patient of a health care appointment and indicating the positive feedback result the medication adherence has had in the bio-metric telemetry and providing by the at least one processor and the at least one memory the health care provider system a summary of bio-metric telemetry data set, medication adherence data set and positive feedback prior to the health care appointment.

In a further embodiment, a system comprises at least one processor and at least one memory, wherein the at least one processor and the at least one memory performs at least one of: receives by the at least one processor and the at least one memory a bio-metric telemetry data set from a patient, receives by the at least one processor and the at least one memory a medication adherence data set from the patient, notifies by the at least one processor and the at least one memory a health care provider system of at least one potential alarm based on the bio-metric telemetry data set and the medication adherence data set, notifies by the at least one processor and the at least one memory the patient utilizing positive feedback of the bio-metric telemetry data set and the medication adherence data set, wherein the positive feedback is an affirmation communication from the health care provider system that indicates medication adherence has a positive feedback result in the bio-metric telemetry, notifies by the at least one processor and the at least one memory the patient of a health care appointment and indicates the positive feedback result the medication adherence has had in the bio-metric telemetry and provides by the at least one processor and the at least one memory the health care provider system a summary of bio-metric telemetry data set, medication adherence data set and positive feedback prior to the health care appointment.

In another embodiment, a non-transitory computer readable medium comprises instructions that when read by at least one processor and at least one memory and at least one memory performs at least one of: receiving by the at least one processor and the at least one memory a bio-metric telemetry data set from a patient, receiving by the at least one processor and the at least one memory a medication adherence data set from the patient, notifying by the at least one processor and the at least one memory a health care provider system of at least one potential alarm based on the bio-metric telemetry data set and the medication adherence data set, notifying by the at least one processor and the at least one memory the patient utilizing positive feedback of the bio-metric telemetry data set and the medication adherence data set, wherein the positive feedback is an affirming communication from the health care provider system indicating that the medication adherence has a positive feedback result in the bio-metric telemetry, notifying by the at least one processor and the at least one memory the patient of a health care appointment and indicating the positive feedback result the medication adherence has had in the bio-metric telemetry and providing by the at least one processor and the at least one memory the health care provider system a summary of bio-metric telemetry data set, medication adherence data set and positive feedback prior to the health care appointment.

DETAILED DESCRIPTION

It may be readily understood that the components of the present application, as generally described and illustrated in the figures herein, may be arranged and designed in a wide variety of different configurations. Thus, the following detailed description of the examples of a method, apparatus, and system, as represented in the attached figures, is not intended to limit the scope of the application as claimed, but is merely representative of selected examples of the application.

The features, structures, or characteristics of the application described throughout this specification may be combined in a suitable manner in one or more examples. For example, the usage of the phrases example, examples, some examples, or other similar language, throughout this specification refers to the fact that a particular feature, structure, or characteristic described in connection with the example may be included in at least one example of the present application. Thus, appearances of the phrases example, examples, in some examples, in other examples, or other similar language, throughout this specification does not necessarily refer to the same group of examples, and the described features, structures, or characteristics may be combined in a suitable manner in one or more examples.

Currently, healthcare provider and patient communication systems are rigid and largely not adjustable by the patient to aide in effective communication. The present disclosure provides possible solutions to allow adjustable technology enabled communications pathways between healthcare providers and patients to meet the communication preferences of the patient.

Figure 1:
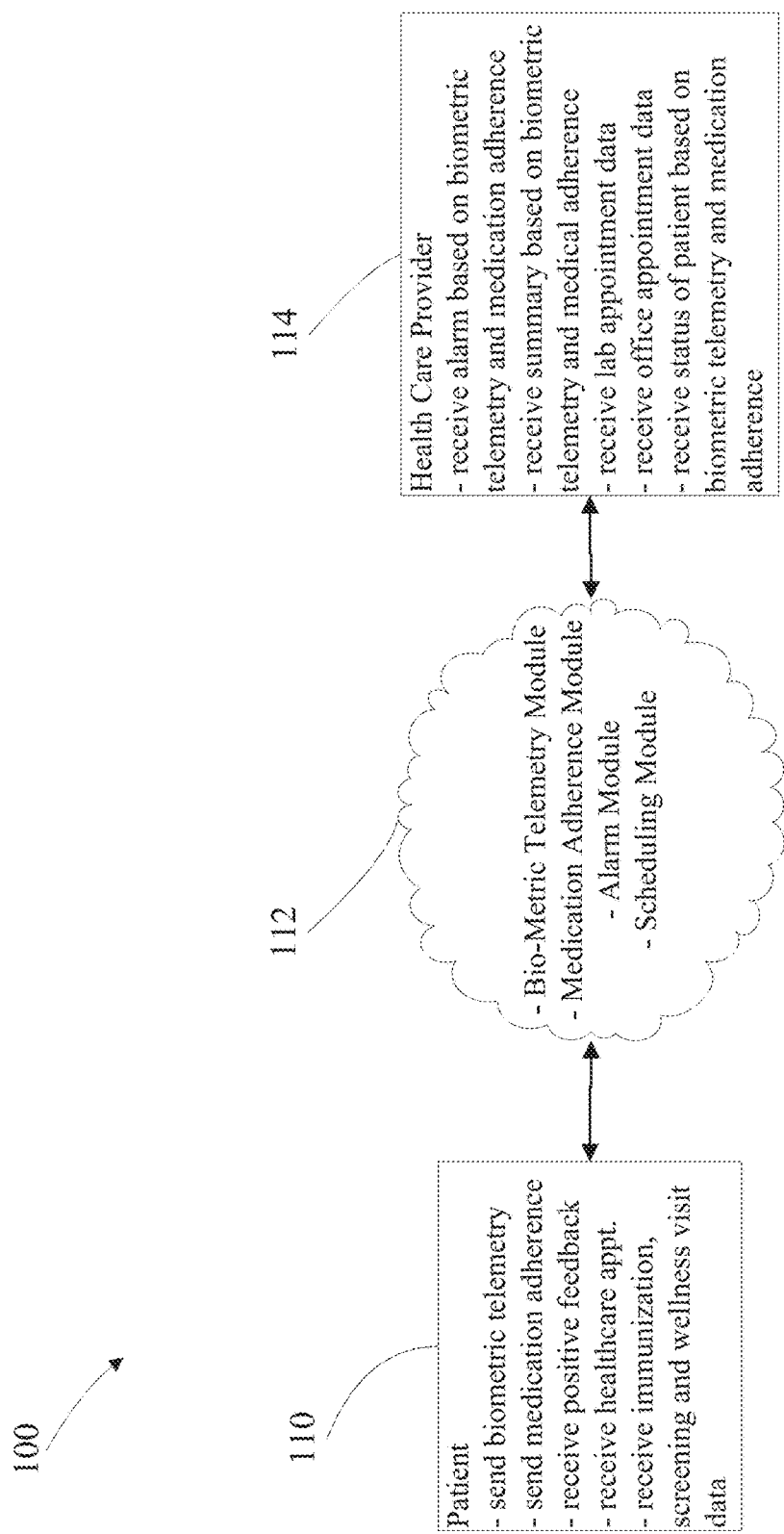
FIG. 1 depicts a first example system in accordance with one embodiment of the disclosure.

Computer System FIG. 1 illustrates the system architecture for an exemplary communication system 100 with which the current disclosure may be implemented. The exemplary computer system of FIG. 1 is for descriptive purposes.

Communication system 100 includes a patient communication system 110, that includes at least one processor and at least one memory (not shown) that is able to send at least one of biometric telemetry data set and medication adherence data set to a cloud based system 112, that includes at least one processor and at least one memory (not shown) and to receive from the cloud based system at least one of positive feedback, healthcare appointments, immunization, screening and wellness visit data to the patient. The cloud based system 112 may comprise a bio-metric telemetry module, which receives and interprets the biometric telemetry data set, a medication adherence module which receives and interprets the patient dosing, an alarm module tied to preset conditions from the biometric telemetry data set and the medication adherence dataset and a scheduling module which coordinates communication and physical or virtual/electronic interactions with the patient. The health care provider system 114, includes at least one processor and at least one memory (not shown) is able to perform at least one of receive alarms based on biometric telemetry and medication adherence, receive lab appointment data and office appointment data and receive the status of the patient based on the biometric telemetry data set and medication adherence data set.

Figure 8:
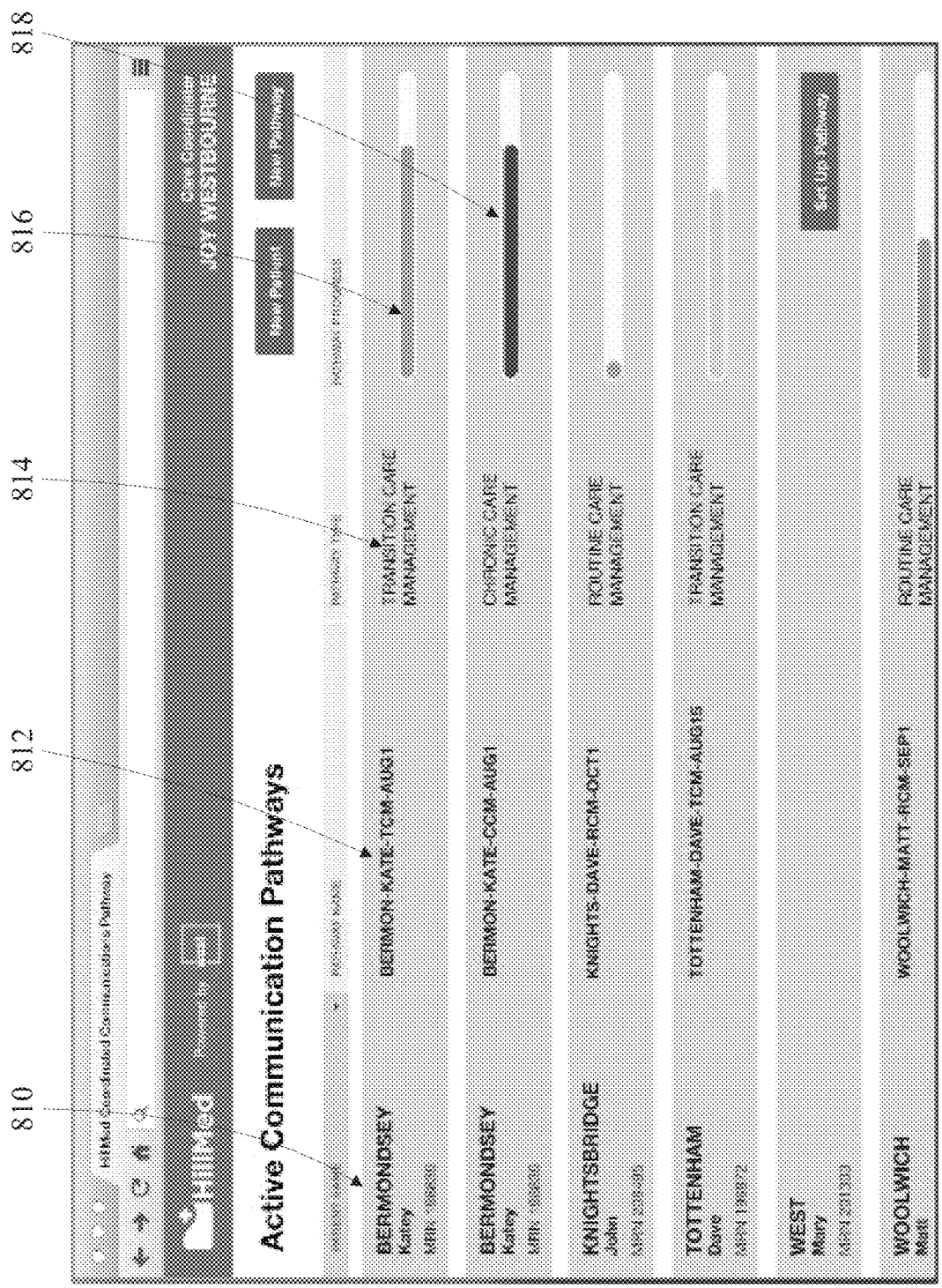
FIG. 8 depicts an example active technology enabled communications pathways overview.
Figure 9:
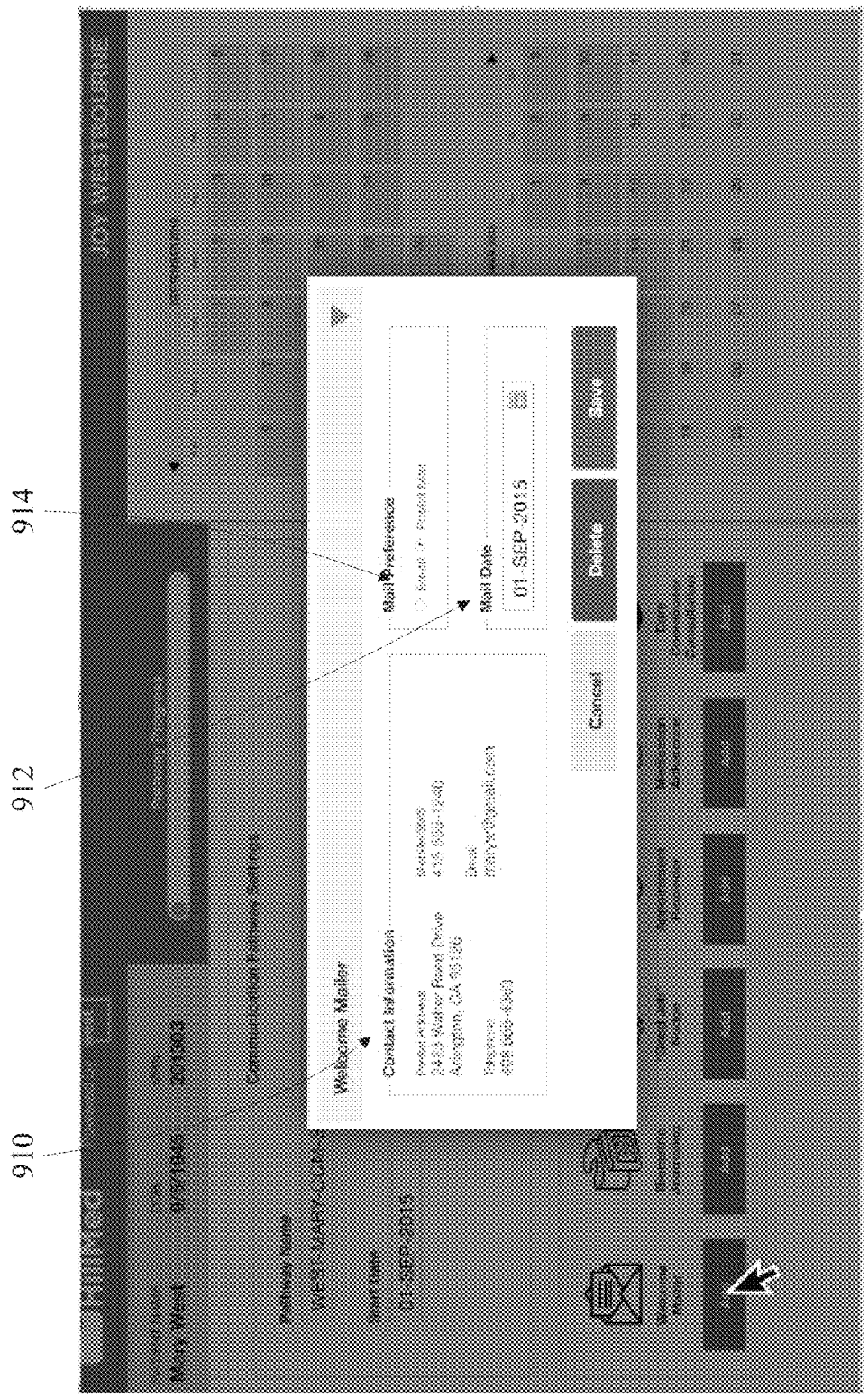
FIG. 9 depicts an example patient preferences selection.
Figure 10:
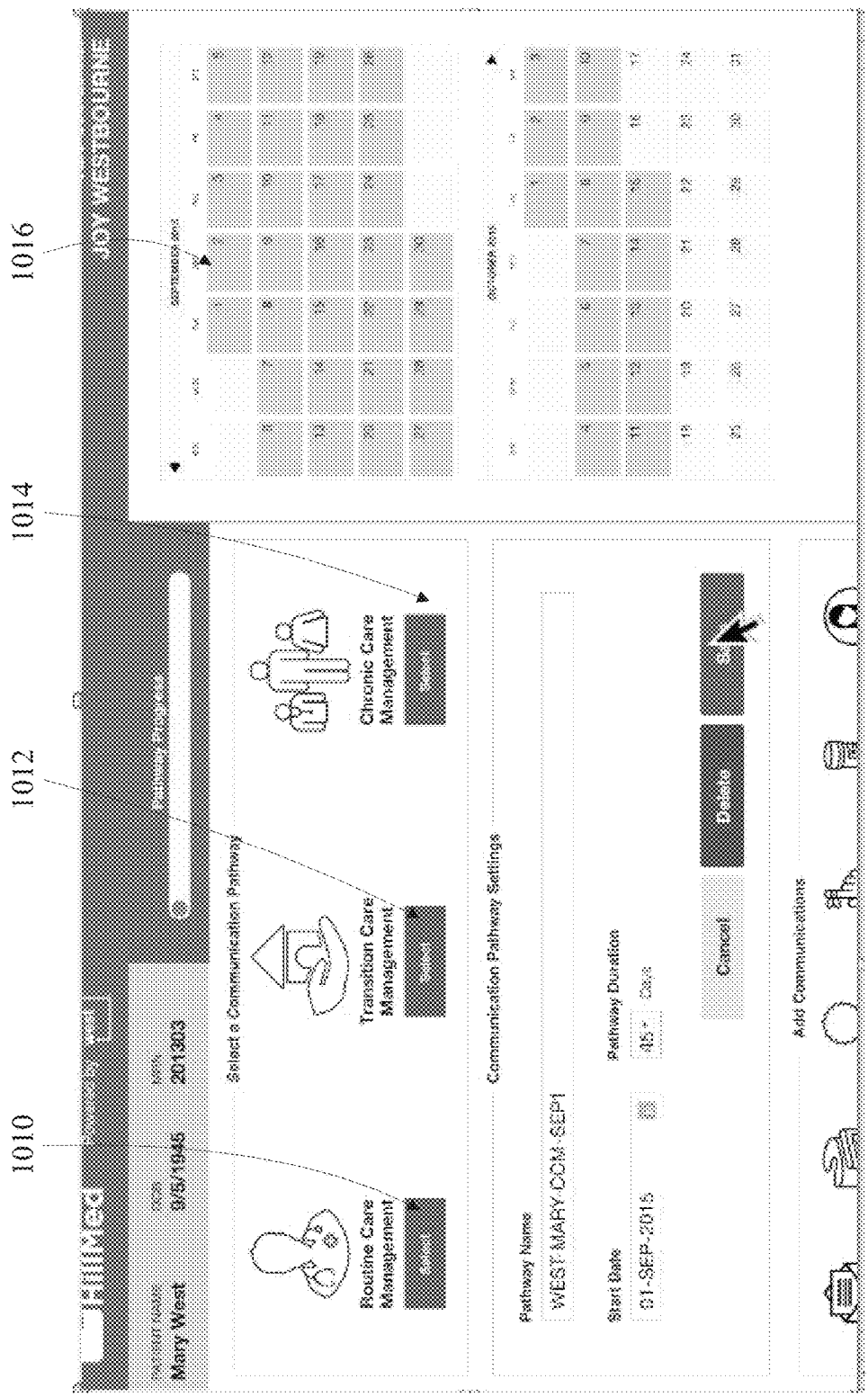
FIG. 10 depicts an example technology enabled communications pathway selection and setup.

The technology enabled communications pathway system 112 is cloud-based and enables organizations to align patient communication and engagement with medical and clinical guidelines or a plan of care. FIG. 8 shows an overview technology enabled communications pathway interface having the patient name 810, the name of the pathway 812, the type of care management 814 and patient progress 816. The application contains condition-specific and outcome-focused libraries of communication interventions that a healthcare provider can subscribe to. For example, an organization may subscribe to the system library for hypertension chronic care management to facilitate a care management program for risk-stratified hypertensive patients. An organization may also subscribe to the system library for transition care management to facilitate patient engagement post-discharge to reduce hospital readmissions. Similar libraries may exist for major chronic conditions and for less complex routine care management to reduce gaps in care such as wellness visits, screenings, and immunizations. In lieu of a cloud based system, the system may also utilize a server, server farm, computer, mobile processor or any processor linked to a memory. An example patient setup interface is shown in FIG. 9, where the patient contact information is input 910, mail date 912 and the patient mail preference 914. An example pathway interface is shown in FIG. 10 which allows selection of routine care management 1010, transition care management 1012, chronic care management 1014 and the linked calendar 1016.

Figure 11:
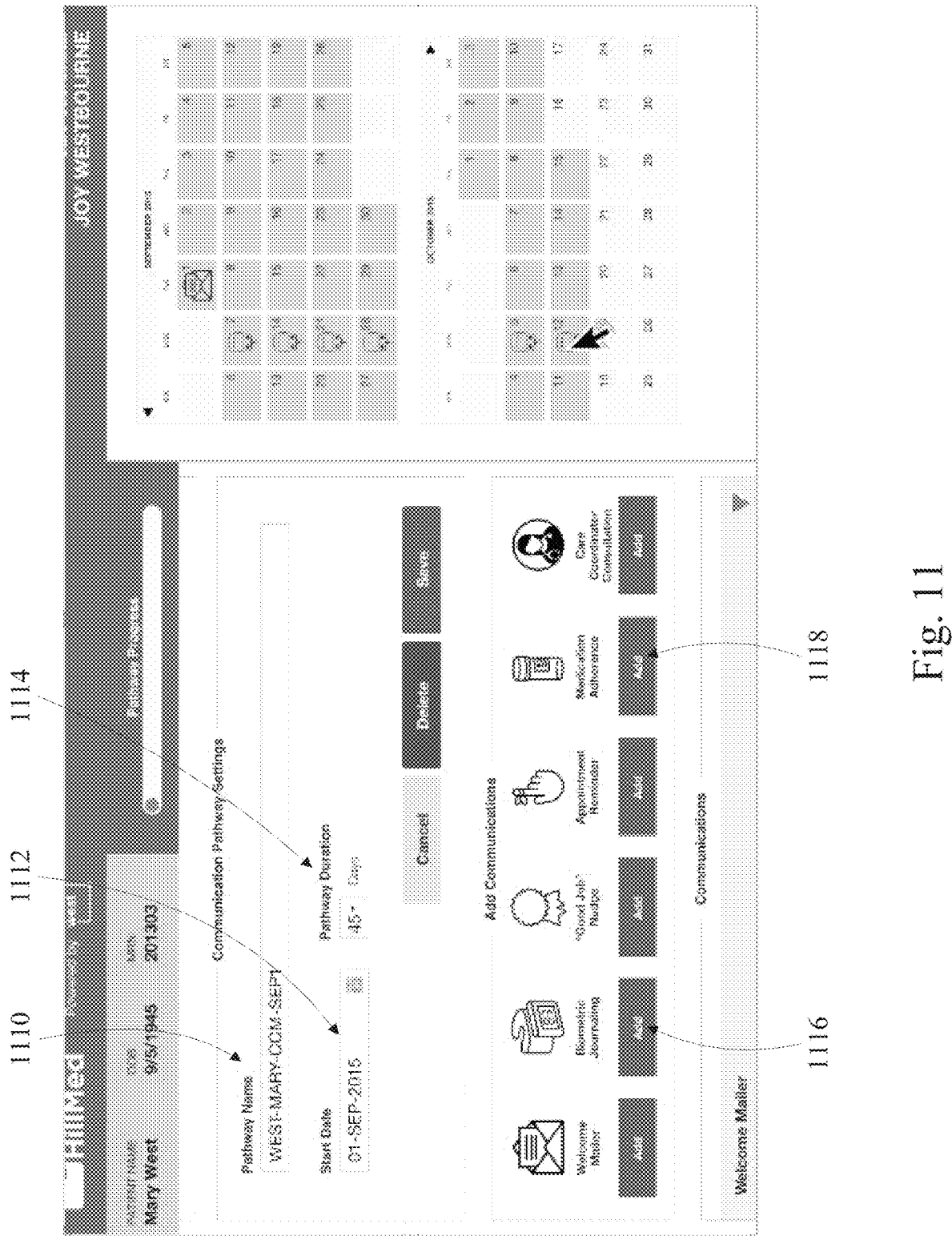
FIG. 11 depicts an example technology enabled communications pathway date setup.
Figure 12:
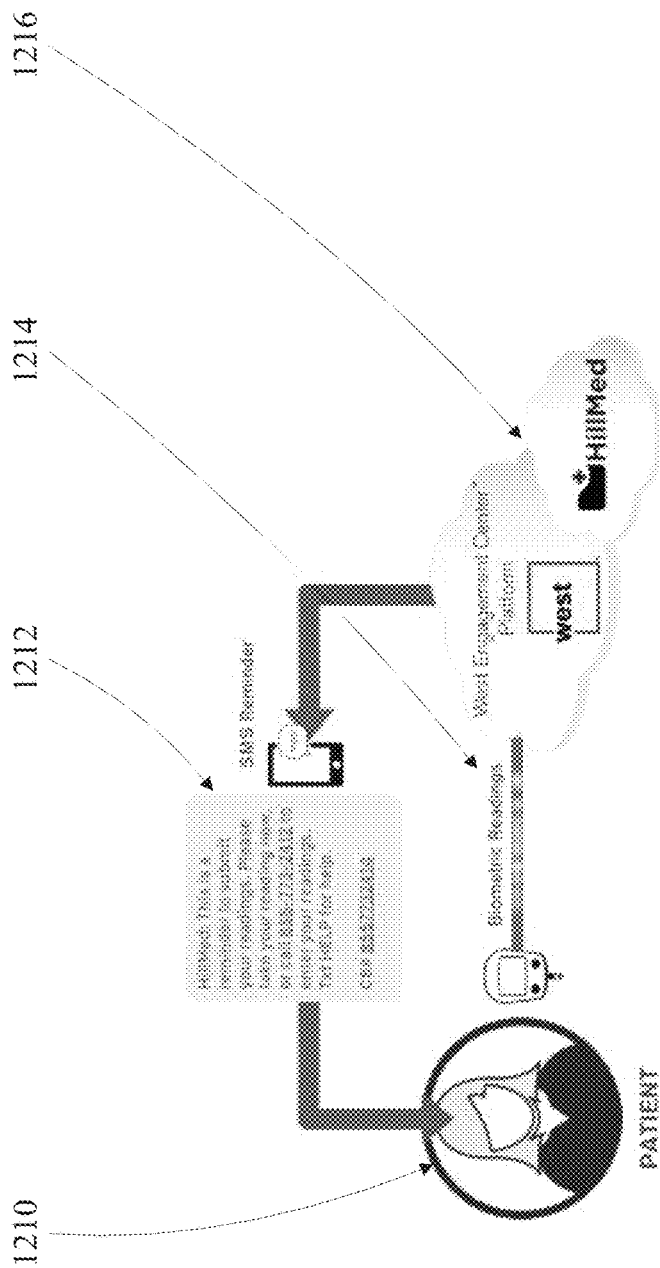
FIG. 12 depicts an example biometric reminder.
Figure 13:
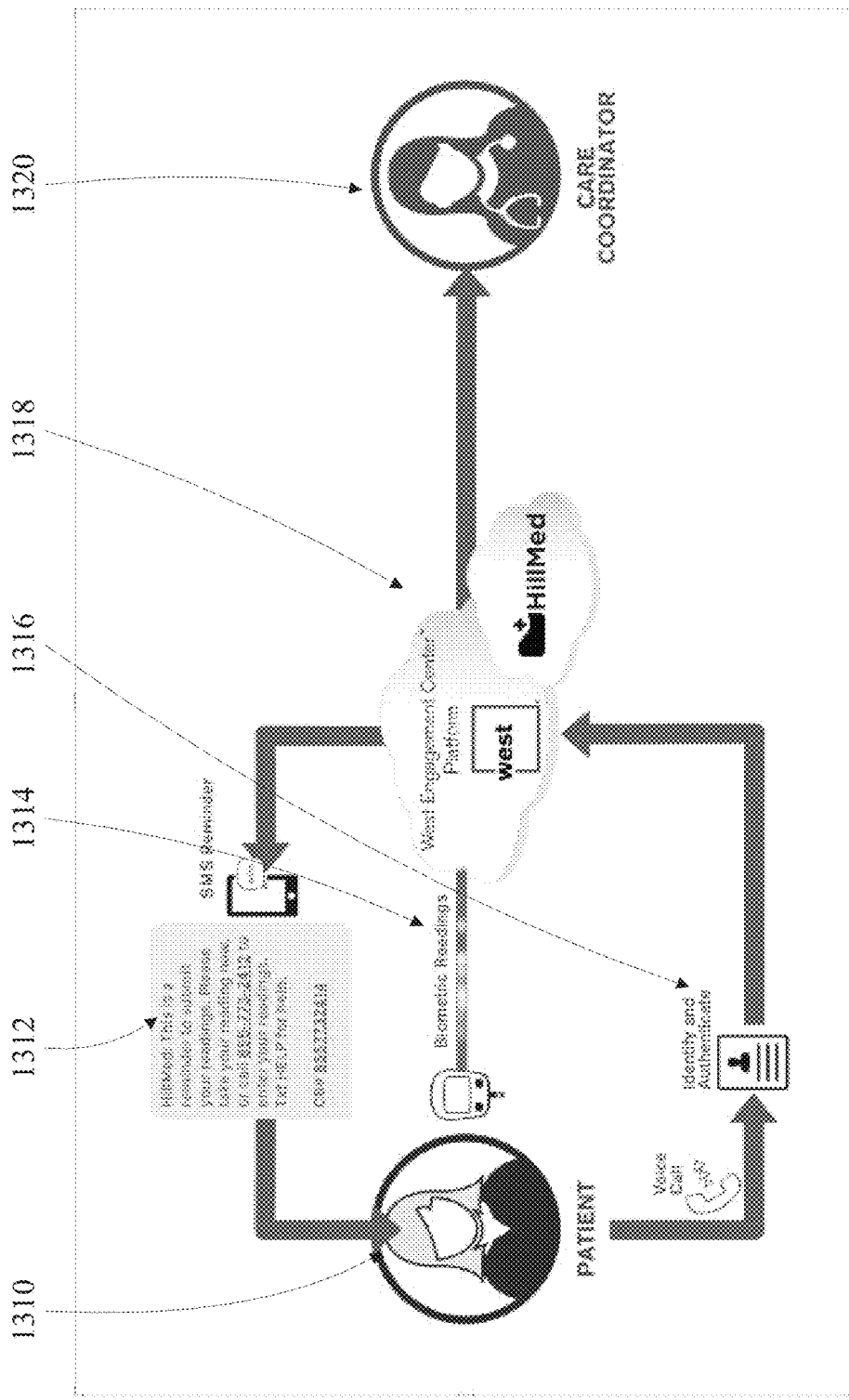
FIG. 13 depicts an example biometric communication flow.

A provider may assign a library to the patient based on the patients diagnosis, biometric data, medication and lifestyle. An example biometric setup is shown in FIG. 11, the patient name 1110, start date 1112 and pathway duration 1114. The library may contain a set of communication interventions, which are designed and sequenced to perform tasks common to that particular chronic condition or outcome. It is envisioned that the technology enabled communications pathway system (112 FIG. 1) ingests the biometric data set, mediation adherence dataset, surveys pertaining to lifestyle and diagnosis and determines which components portions of the library are most pertinent to the patient based on the ingested data. A first example biometric dataflow is shown in FIG. 12, the patient 1210 takes a biometric reading 1214 in response to an SMS message 1212, where the data is sent from the biometric device to the cloud 1216. An alternate biometric dataflow is shown in FIG. 13, where the patient 1312 receives a reminder 1312 from the communication system, a biometric sample is taken 1314 which is sent to the cloud 1318. Alternately, a voice call may be identified and authenticated 1316, the result of the biometric sample is sent to the healthcare provider 1320.

Figure 16:
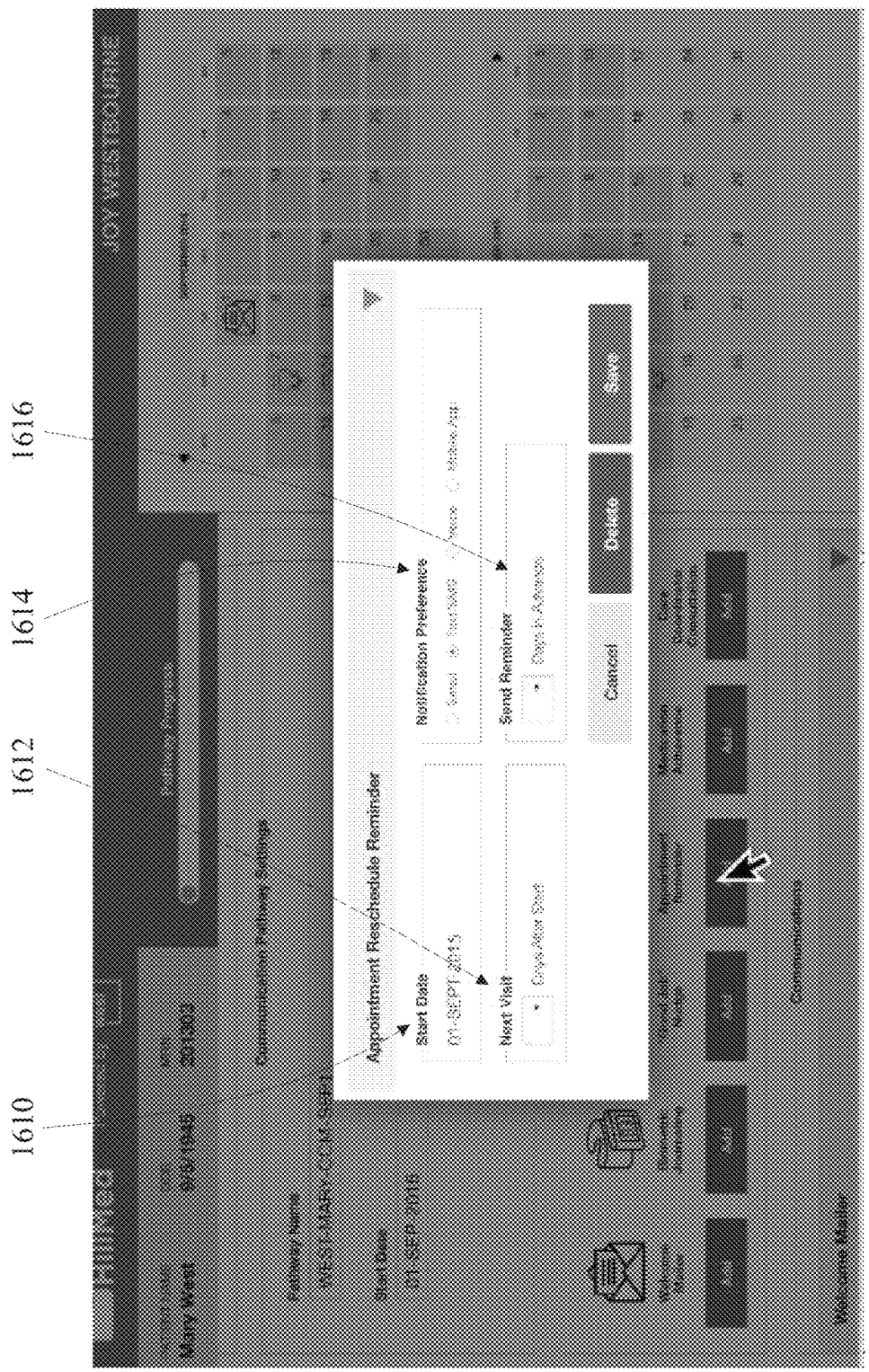
FIG. 16 depicts an example appointment and notification setup.

To enable provider flexibility and drive greater patient-centeredness, the system is customizable with respect to patient selection of communication channel such as email, SMS, voicemail or mail such that communication interventions can be added or omitted, FIG. 16 appointment interface showing the notification preferences 1614. Various parameters of the communication intervention such as sequence, duration and frequency, can be modified by the healthcare provider, FIG. 16 showing the start date 1610, visitation delta dates 1612 and the reminder times 1616, resulting in a customized system from both the standpoint of the patient with respect to communication channel and to the healthcare provider with respect to content and timing.

Greater patient interaction in transition from the hospital to home is enabled by providing a Web based post-discharge survey that the patient assesses viewpoints and concerns. Emergency room diversion is accomplished by utilizing care reminders so that small problems do not become emergencies and also provides medication reconciliation and addresses adherence issues, sends appointment and lab reminders and sends the patient instructions for preparation for lab work.

The system may also send communications from the health care provider system to the patient pertaining to immunization, screening and wellness visit reminders and may provide lifestyle and health education based on the inputs from the biometric tele-monitoring data set, data input based on medication and office and lab visit information.

Condition-specific and outcome-focused libraries of engagement to address specific disease states or wellness objectives over time may be used. Prescribed communications may be delivered based on the patient's communication preference, such as voice, text, Web, mobile or remote monitoring device. An example next visit for the patient may be adjusted by the appointment interface (1612 FIG. 16) to reduce administrative effort and enable staff to handle larger patient panels. Alarms and dashboards provide insight into escalated interventions for patients and update patient records with information gathered during engagement. An example alarm is shown in FIG. 8, the bar in red 818.

Figure 2:
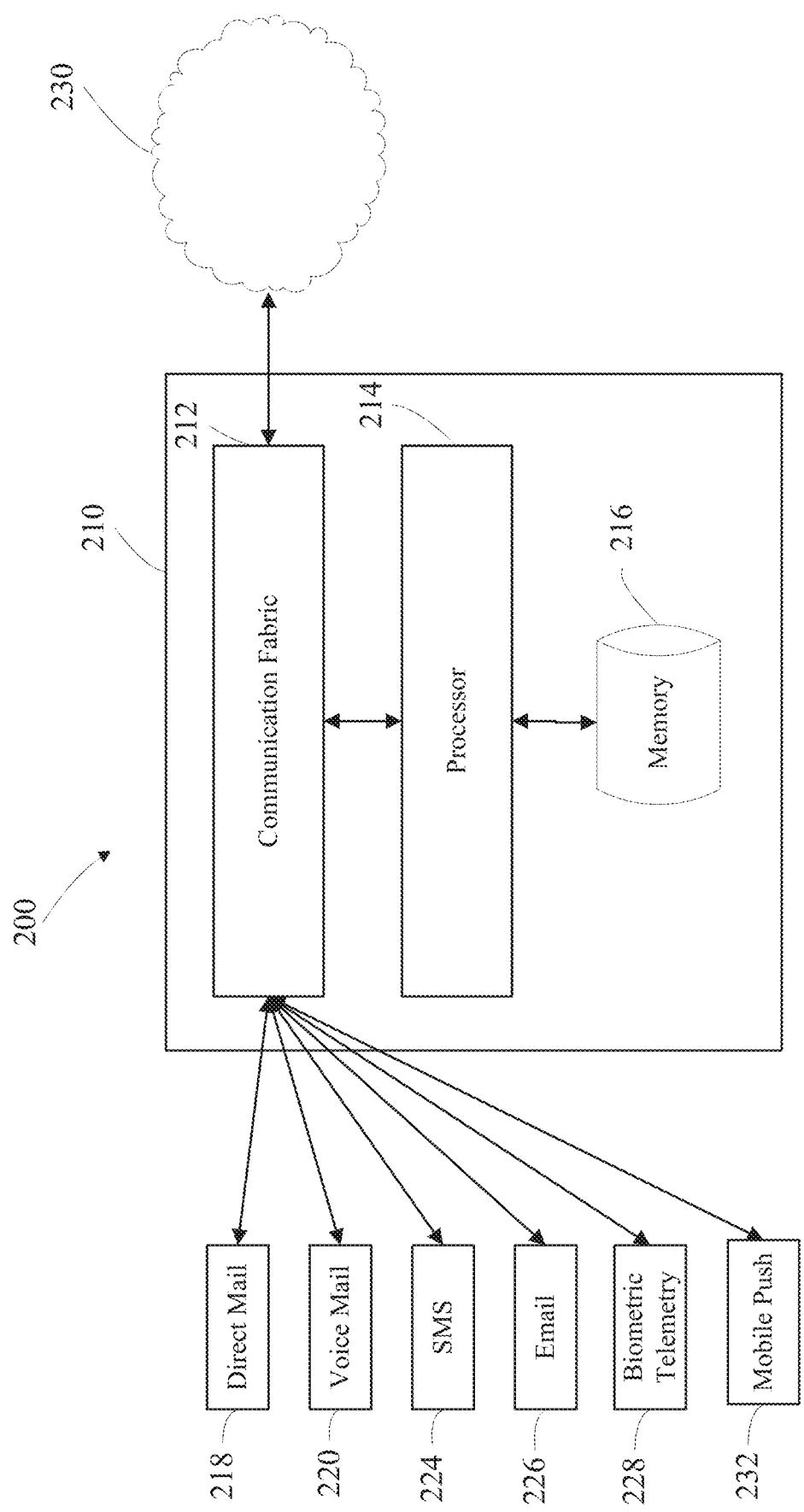
FIG. 2 depicts an example technology enabled communications pathway in accordance with one embodiment of the disclosure.

Computer System FIG. 2 illustrates a communication system 200 with which the current disclosure may be implemented. The conferencing system 210, has a communication fabric 212 connected to at least one processor 214 which in turn is connected to at least one memory 216 which contains instructions to control the processor and the communication fabric. The communication fabric 212 may be connected to direct mail 218, voice mail 220, short message system 224, email 226, mobile push notification 232, biometric telemetry transmitter 228 and the like. The preference as to how the communication fabric is used is specified in notification preference (1614 FIG. 16). The preference is chosen by the patient, but input into the interface by the healthcare provider. The communication fabric 212 is also connected to the internet, network or cloud 230. Mobile push notification 232 is the delivery of information from the technology enabled communications pathway to a mobile device without a specific request from the patient. Mobile push may be the selection of the patient for a communication channel and preference.

Figure 3:
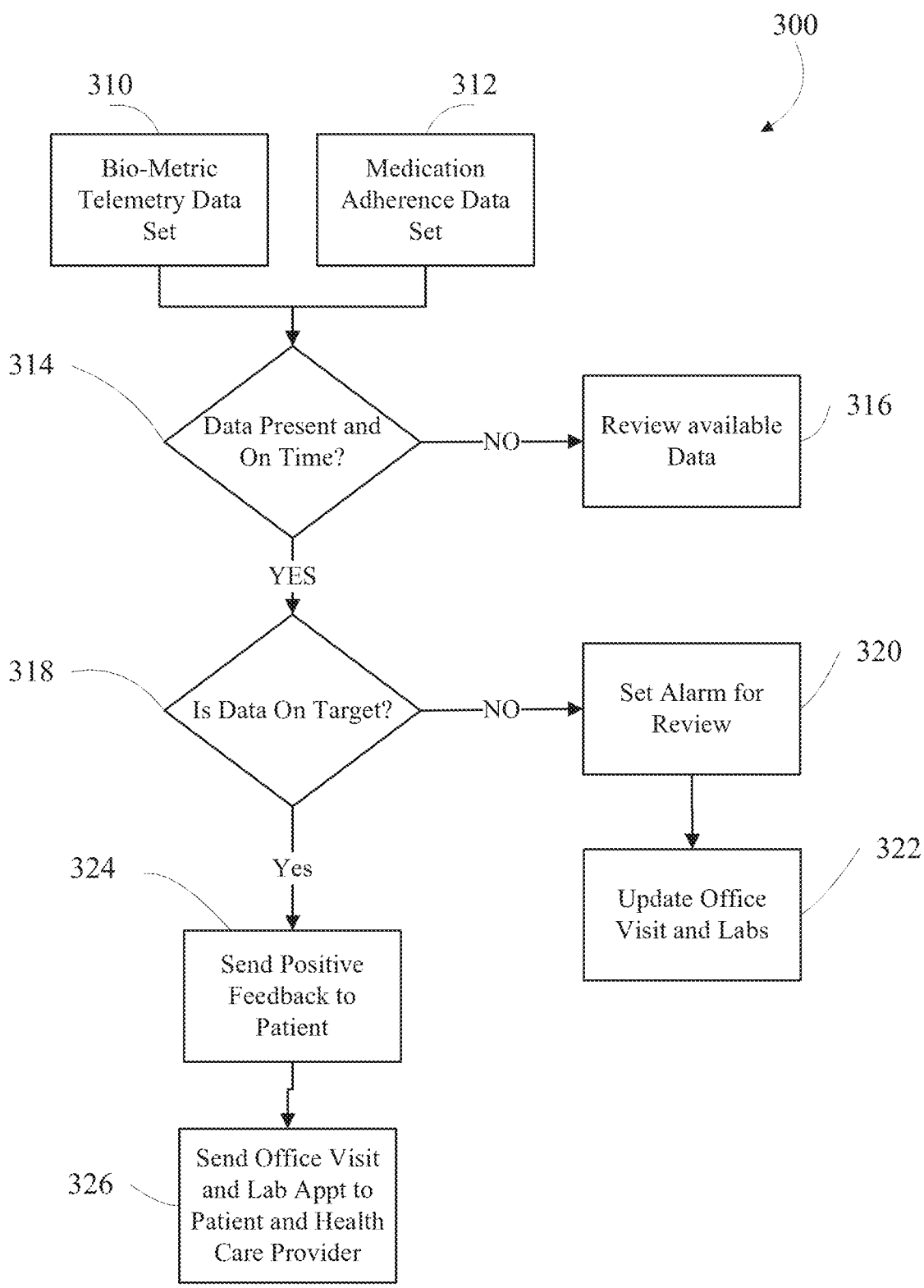
FIG. 3 depicts an example logic flow in accordance with one embodiment of the disclosure.
Figure 14:
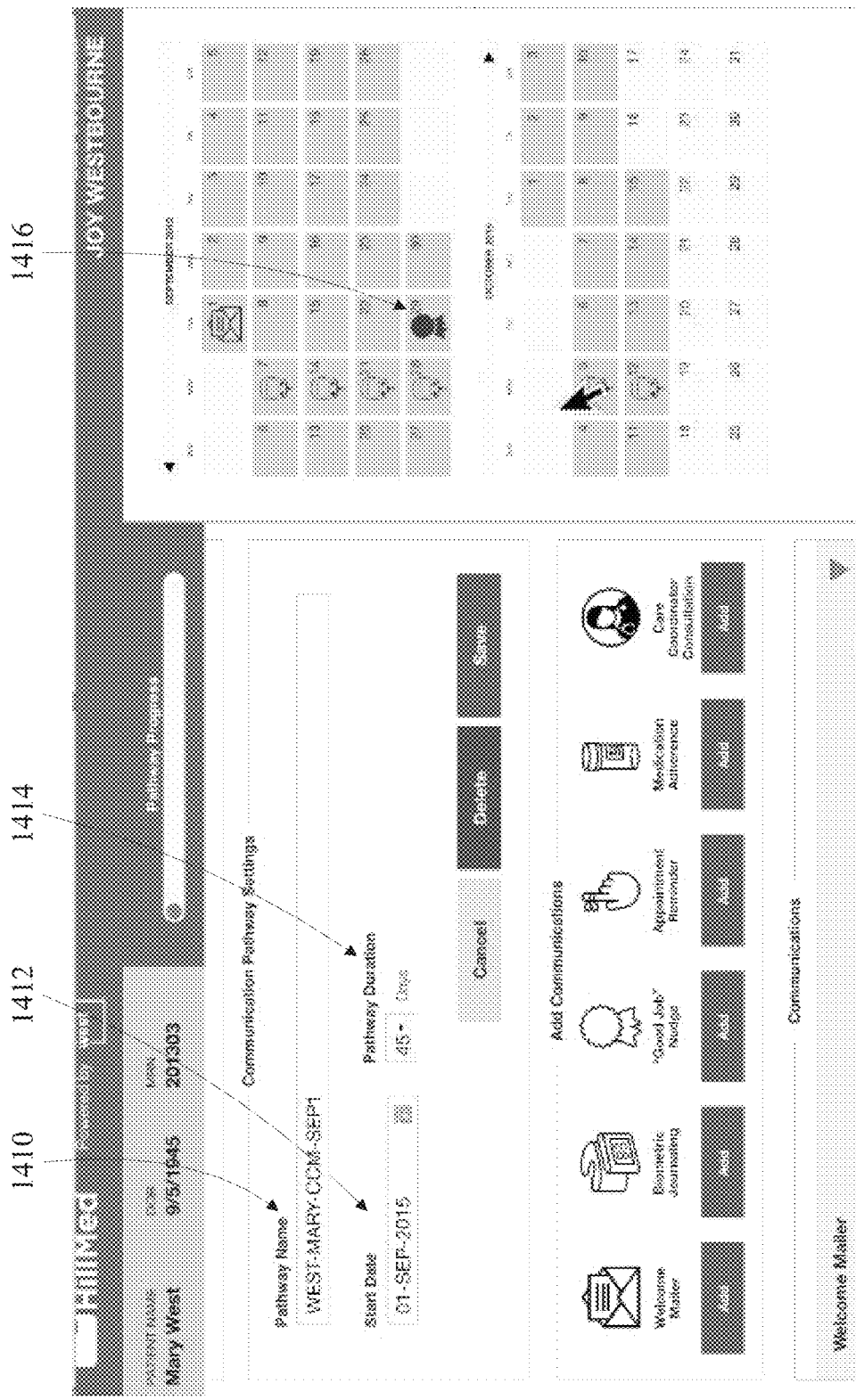
FIG. 14 depicts an example positive feedback calendar.
Figure 15:
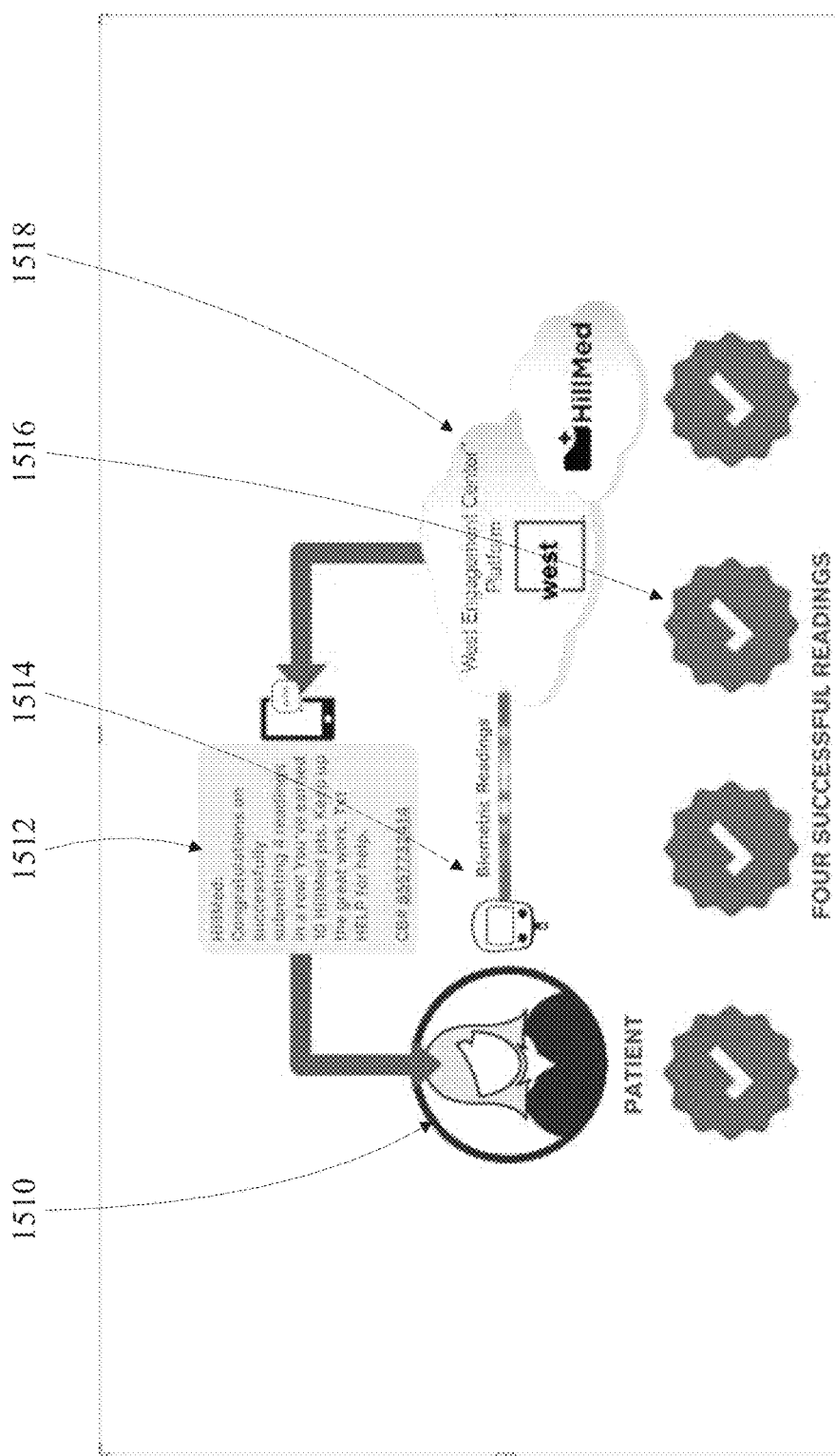
FIG. 15 depicts an example positive feedback flow.

Referring now to FIG. 3, an example logic flow diagram is depicted. A patient communication (110 FIG. 1) sends 310 bio-metric telemetry data sets and medication adherence data sets 312 to the cloud (112 FIG. 1). The system determines 314 whether the data is present and on time, if it is not then the data is reviewed 316 for possible anomalies. If the data is present and on time, a determination 318 is made as to whether the data is on target. If the data is not on target a review is done to determine whether an alarm is set 320 and if yes, then office and lab visits may be updated 322. If the data is on time, present and on target positive feedback is sent 324 to the patient and the health care provider system along with office and lab appointment 326. FIG. 14 shows an example pathway setting for positive feedback, the pathway name 1410, start date 1412, pathway duration 1414 and associated calendar 1416 are set by the healthcare provider. FIG. 15 shows an example where the patient 1510 takes a biometric sample 1514. The positive message 1512 is sent to the patient from the cloud 1518. The positive message 1512 is sent in response to four successful meetings 1516.

A technology enabled communications pathway (system) can be used to manage patient populations across a care continuum, an example interface is shown in FIG. 10, where the continuum includes routine care management 1010, transition care management 1012 and chronic care management 1014. In the case of chronic care management, communicating routine tasks such as biometric journaling, helps organizations achieve greater scale and capacity by significantly increasing patient-to-care coordinator ratios and enabling them to spend more time with patients who require the extra care, thereby more efficiently managing to better patient outcomes. FIG. 8, shows an overview interface that includes the patient 810, pathway 814 and progress 816 allowing an overview of a number of patients, under the patient name 810.

The system offers communications in a bi-directional manner and is artificially intelligent and delivers multi-channel communication to the patient in their preferred channel of choice such as direct mail, voice, SMS, email and the like shown as an interface in FIG. 16 notification preference 1614. The bi-directional manner of communication is shown as an example interface in FIG. 13 between the patient 1310 and the health care provider system 1320.

The system collects patient intervention data and updates the electronic medical record (EMR) or healthcare system across participating providers, enabling them to improve patient engagement, deliver quality coordinated care and reduce costs. Dashboard view of interactions with patients is provided to ease overview.

Figure 4:
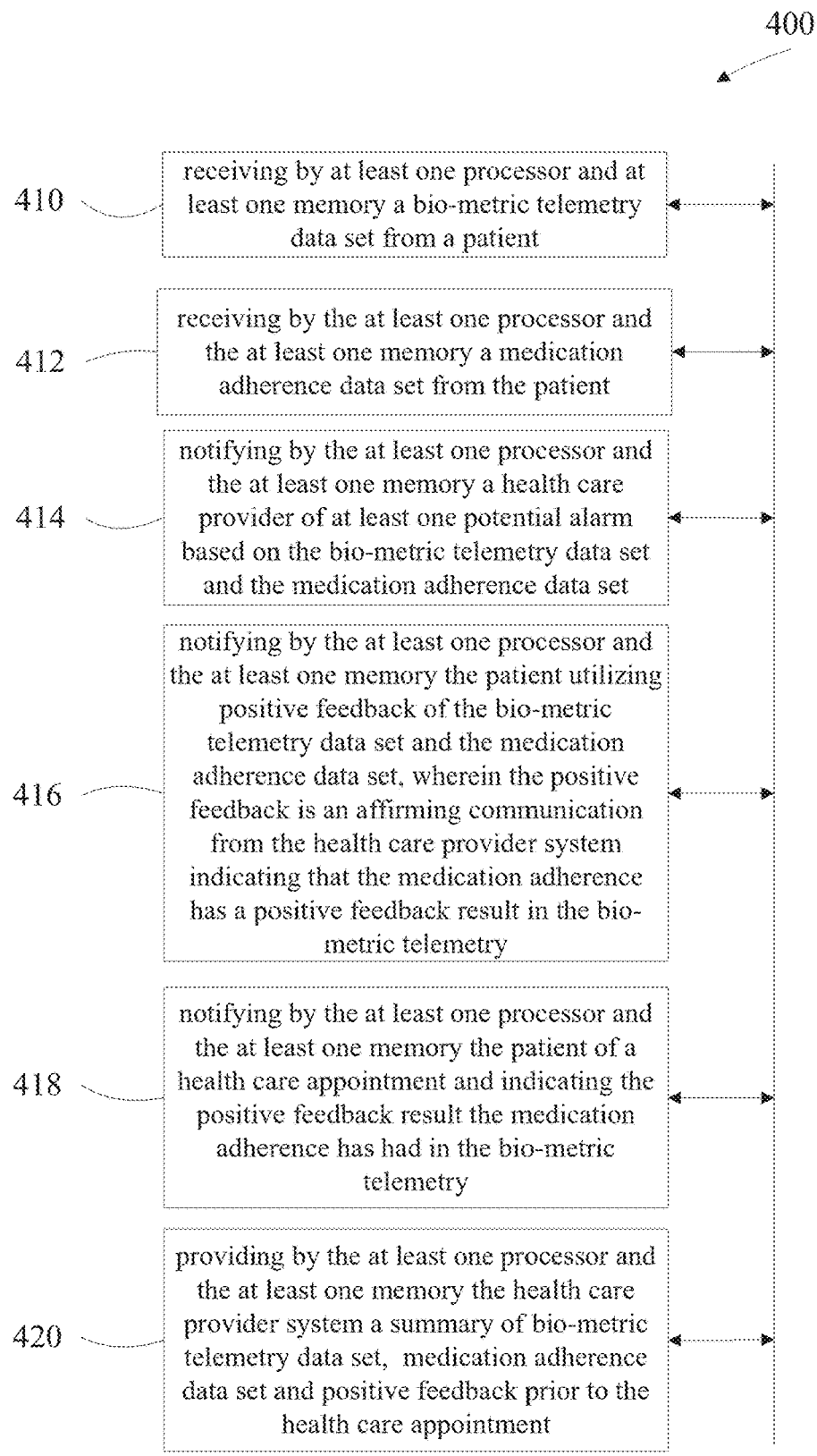
FIG. 4 depicts a first example method in accordance with one embodiment of the disclosure.
Figure 17:
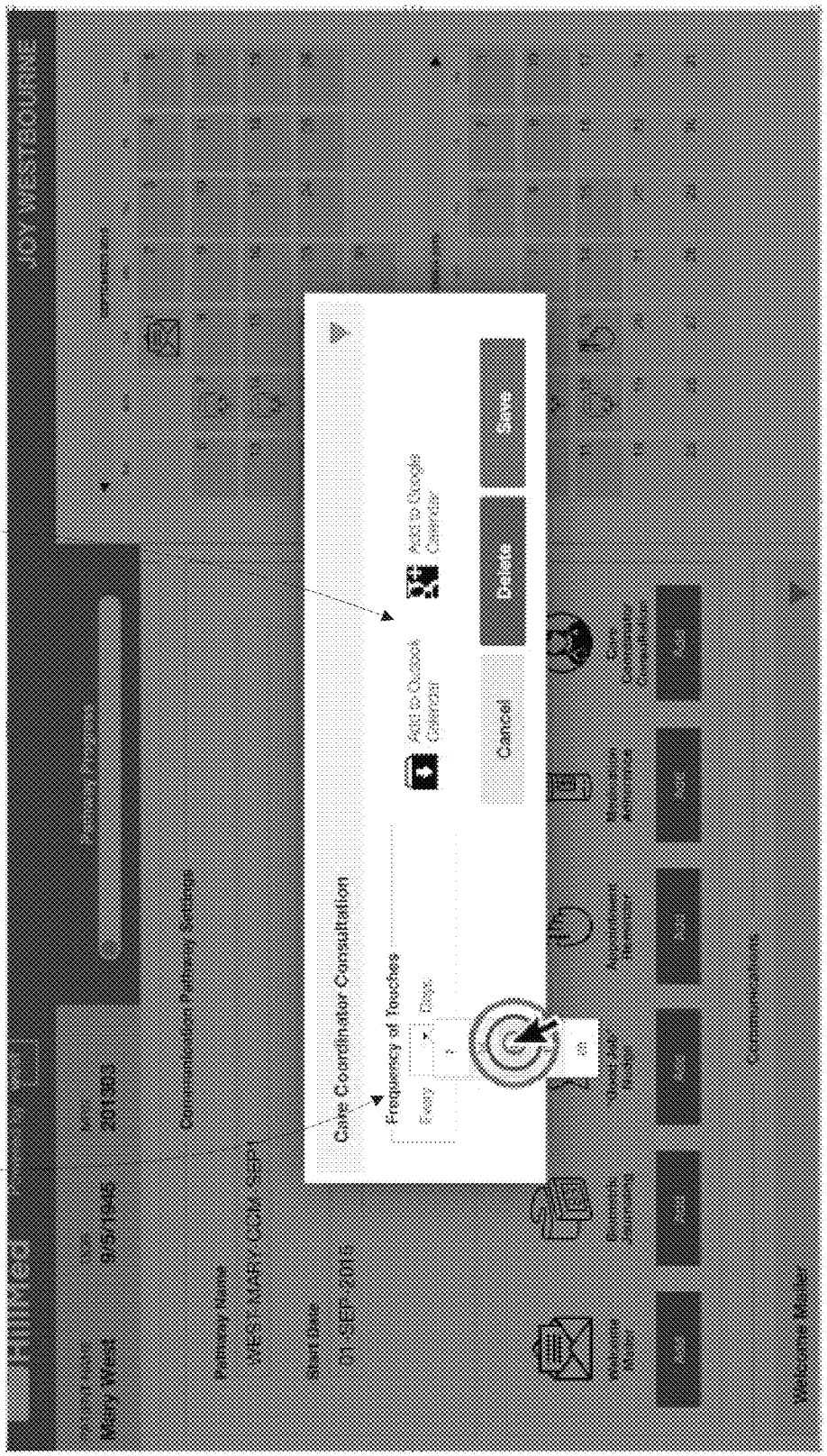
FIG. 17 depicts an example appointment calendaring.

Referring now to FIG. 4, a method, comprising, receiving 410 by at least one processor and at least one memory a bio-metric telemetry data set from a patient. Bio-metric telemetry comprises sensors for a specific medical signal, such as heart rate, temperature, glucose level and the like, a transmitter, receiver and signal output unit. The method also comprises receiving 412 by the at least one processor and the at least one memory a medication adherence data set from the patient, the medication adherence data may take the form of web interaction or feedback from a dispenser and notifying 414 by the at least one processor and the at least one memory a health care provider system of at least one potential alarm based on the bio-metric telemetry data set and the medication adherence data set. The alarm is set when a predetermined level of bio-metric telemetry or medication adherence is crossed. The method also performs notifying 416 by the at least one processor and the at least one memory the patient utilizing positive feedback of the bio-metric telemetry data set and the medication adherence data set, wherein the positive feedback is an affirming communication from the health care provider system indicating that the medication adherence has a positive feedback result in the bio-metric telemetry, notifying 418 by the at least one processor and the at least one memory the patient of a health care appointment and indicating the positive feedback result the medication adherence has had in the bio-metric telemetry and providing 420 by the at least one processor and the at least one memory the health care provider system a summary of bio-metric telemetry data set, medication adherence data set and positive feedback prior to the health care appointment. The positive feedback may take whatever form the patient has set in their preferences. An appointment interface is shown in FIG. 17 where the frequency of contact 1710 is entered and a calendar input is chosen 1712. The calendar input 1712 has as one of its capabilities the ability to modify an upcoming calendar event, align the calendars and push both a mobile notification 232 and export the calendar of events to a common calendar format.

Figure 5:
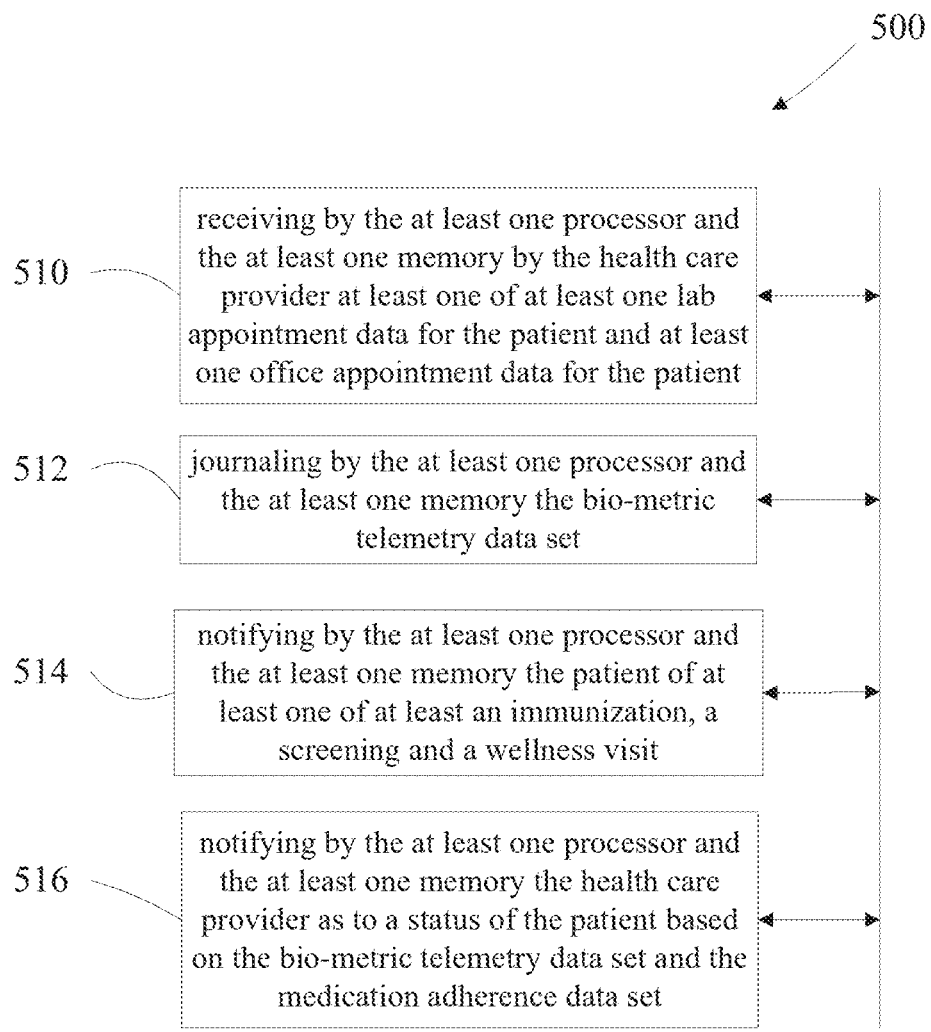
FIG. 5 depicts a second example method in accordance with one embodiment of the disclosure.
Figure 20:
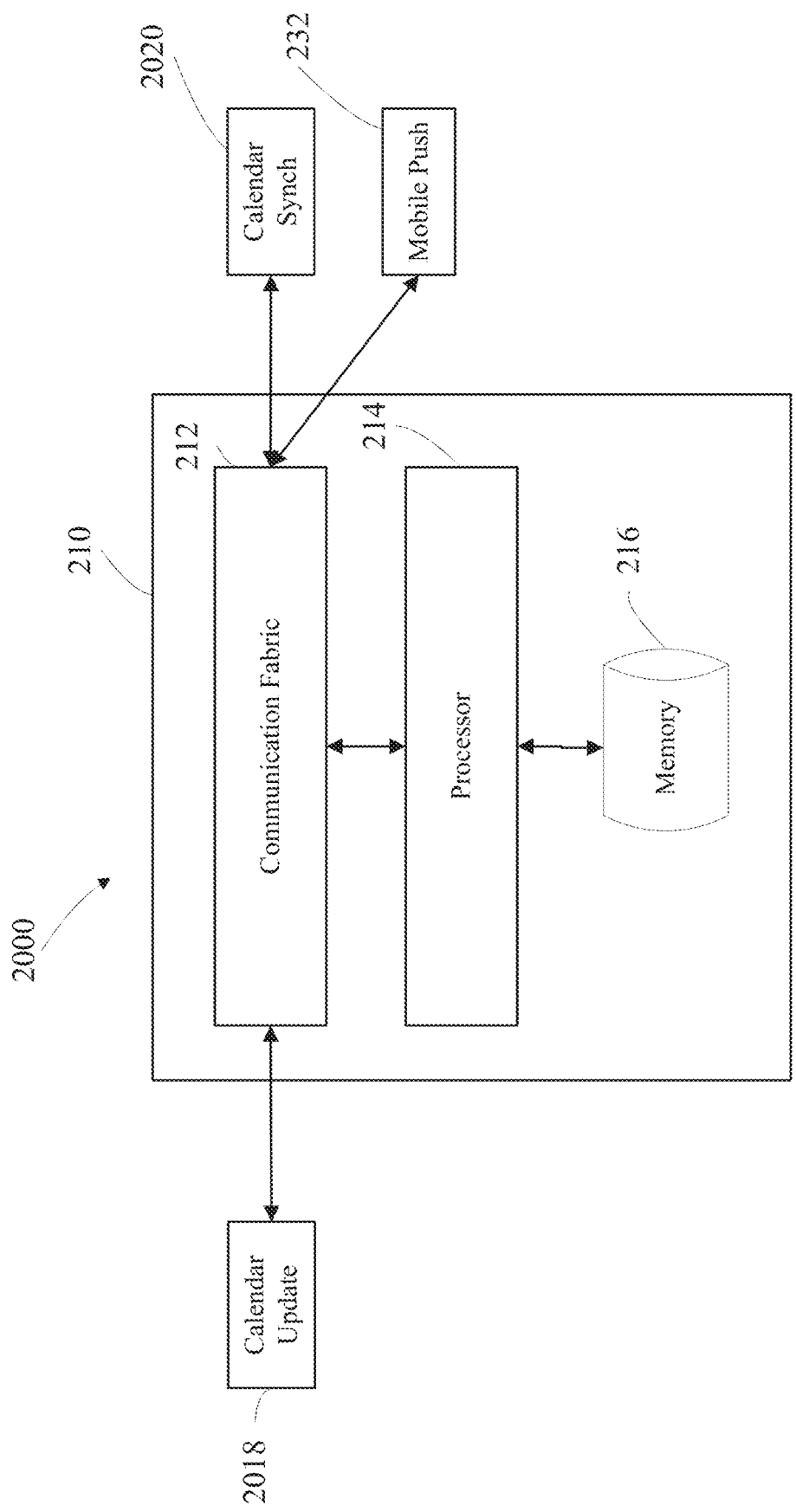
FIG. 20 depicts a second example technology enabled communications pathway in accordance with one embodiment of the disclosure.

Referring now to FIG. 5, the method of FIG. 4 may further comprise receiving 510 by the at least one processor and the at least one memory by the health care provider system at least one of at least one lab appointment data for the patient and at least one office appointment data for the patient as shown in 1610, 1612, 1614 and 1616 of FIG. 16. The method also comprises journaling 512 by the at least one processor and the at least one memory the bio-metric telemetry data set, the setup for biometric journaling is performed by the healthcare provider, shown as 1116 FIG. 11. The method may also comprise notifying 514 by the at least one processor and the at least one memory the patient of at least one of at least an immunization, a screening and a wellness visit by the healthcare provider (1010 FIG. 10). The method may additionally comprise notifying 516 by the at least one processor and the at least one memory the health care provider system as to a status of the patient based on the bio-metric telemetry data set and the medication adherence data set, which is shown as pathway progress (816 and 818 of FIG. 8). The notification may be based on patient preference by at least one of direct mail, voice, SMS and email, chosen by the patient and uploaded by the healthcare service provider (1614, FIG. 16). A notification sequence, a notification duration and a notification frequency is determined by the health care provider system (1612 and 1616, FIG. 16). Also the health care appointment may comprise at least one upcoming lab appointment and a lab preparation notification may be sent prior to the at least one upcoming lab appointment and the health care appointment comprises at least one upcoming office appointment (1712, FIG. 17). In the case of a calendar mismatch FIG. 20 depicts an example calendar update and synchronization. In this example the calendar is updated 2018, utilizing the communications fabric (212 FIG. 2), processor (214 FIG. 2) and memory (216 FIG. 2) shown in FIG. 2, and resulting in a calendar synchronization 2020 on the patient side with a mobile push notification (232 FIG. 2). In this way the patient may be automatically updated for calendar changes and immediately notified.

The system is envisioned to offer multi-channel, bi-directional communication based on the personalized needs of the patient (1614 FIG. 16). Communication branching input data is reviewed against scheduled and output data according to need and is intervention focused in that patients most at risk receive the most focused attention (816, FIG. 8).

The system prompts the provider for program enrollment and the patient for preferences. Data from the patient is provided by biometric tele-monitoring in addition to tracking of medication adherence (setup at the bottom of FIG. 11) and sending of patient appointment and lab reminders (FIG. 16). Additionally positive notifications may be sent when tele-monitoring, medication adherence and appointments are kept (1512 FIG. 15). In addition lifestyles of the patient may be tracked and suggestions made as to educational interventions based on data inputs and wellness surveys sent to and completed by the patient.

Figure 6:
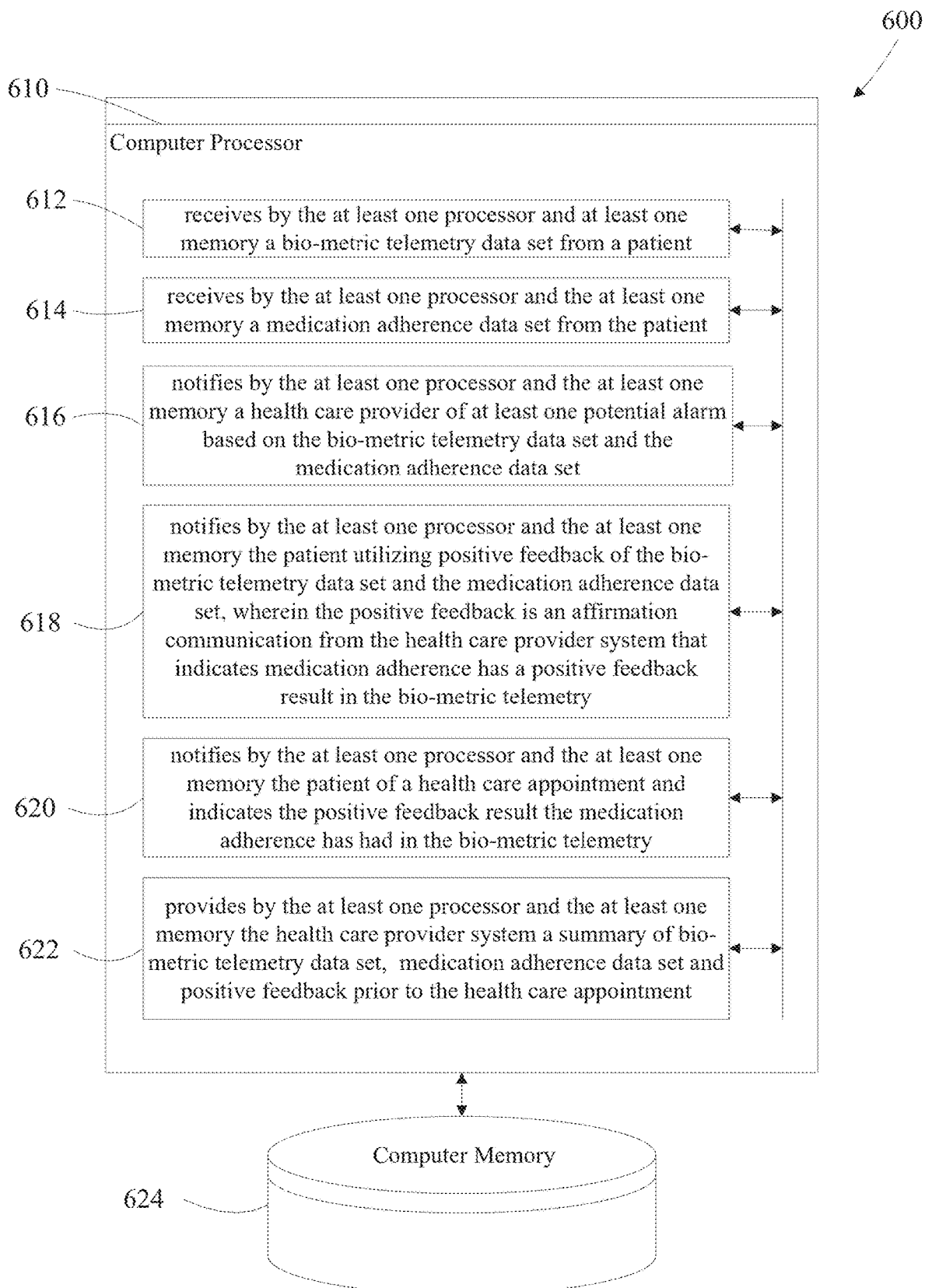
FIG. 6 depicts a second system example in accordance with one embodiment of the disclosure.

FIG. 6 depicts an apparatus comprising at least one processor 610 and at least one memory 624 that receives 612 by the at least one processor and the at least one memory a bio-metric telemetry data set from a patient. The biometric telemetry may be received by a local unit and the information sent either wirelessly or by wired connection to the cloud, a network, a server, computer or the like. The apparatus receives 614 by the at least one processor and the at least one memory a medication adherence data set from the patient, this data set may be received by Web, network, wireless network and the like. An alarm notification 616 (818 FIG. 8) by the at least one processor and the at least one memory a health care provider system of at least one potential alarm based on the bio-metric telemetry data set and the medication adherence data set. The medication adherence data set may be Web based in which the patient updates logs or journals pertaining to the times and effects or side effects of the medications taken. The apparatus also notifies 618 by the at least one processor and the at least one memory the patient utilizing positive feedback of the bio-metric telemetry data set and the medication adherence data set, wherein the positive feedback is an affirmation communication from the health care provider system that indicates medication adherence has a positive feedback result in the bio-metric telemetry (1512 FIG. 15), notifies 620 by the at least one processor and the at least one memory the patient of a health care appointment and indicates the positive feedback result the medication adherence has had in the bio-metric telemetry and provides 622 by the at least one processor and the at least one memory the health care provider system a summary of bio-metric telemetry data set, medication adherence data set (FIG. 8) and positive feedback prior to the health care appointment. The notifications to the health care provider system may be varied as to the patient depending on the healthcare provider communication preferences, an intelligent communication connector is envisioned in which varied communication channels on the patient side may be linked to varied communication channels on the health care professional side.

The apparatus may further comprise receiving by the at least one processor and the at least one memory by the health care provider system at least one lab appointment data for the patient and at least one office appointment data for the patient (FIG. 16) and journaling (1214 FIG. 12) by the at least one processor and the at least one memory the bio-metric telemetry data set. The apparatus may further comprise notifying by the at least one processor and the at least one memory the patient of at least one of at least an immunization, a screening and a wellness visit and notifying by the at least one processor and the at least one memory the health care provider system as to a status of the patient based on the bio-metric telemetry data set and the medication adherence data set (FIG. 8). The notification may be based on patient preference by at least one of direct mail, voice, SMS and email (1614 FIG. 16) and wherein a notification sequence, notification duration and a notification frequency may be determined by the health care provider system (1612 and 1616 FIG. 16).

The system enables greater patient interaction in transition from the hospital to home by providing a post-discharge survey which may be Web, SMS, email or mail based to assess patient viewpoints and concerns and provides emergency room diversion by utilizing care reminders so that small problems do not become emergencies. Medication reconciliation and adherence issues may be tracked (816 and 818 FIG. 8), and appointments, lab reminders and instructions for preparation for lab work may be sent to the patient.

The system may also provide for routine care (1010 FIG. 10) such as sending immunization, screening and wellness visit reminders and may provide lifestyle and health education based on the inputs from the biometric tele-monitoring, data input based on medication and office and lab visit information.

Schedules and sequences of patient care may be determined and tracked (1010, 1012 and 1014 of FIG. 10). Alarms and dashboards (816 and 818 FIG. 8) provide insight into which patients require escalated interventions and update patient records with information gathered during engagement.

Figure 7:
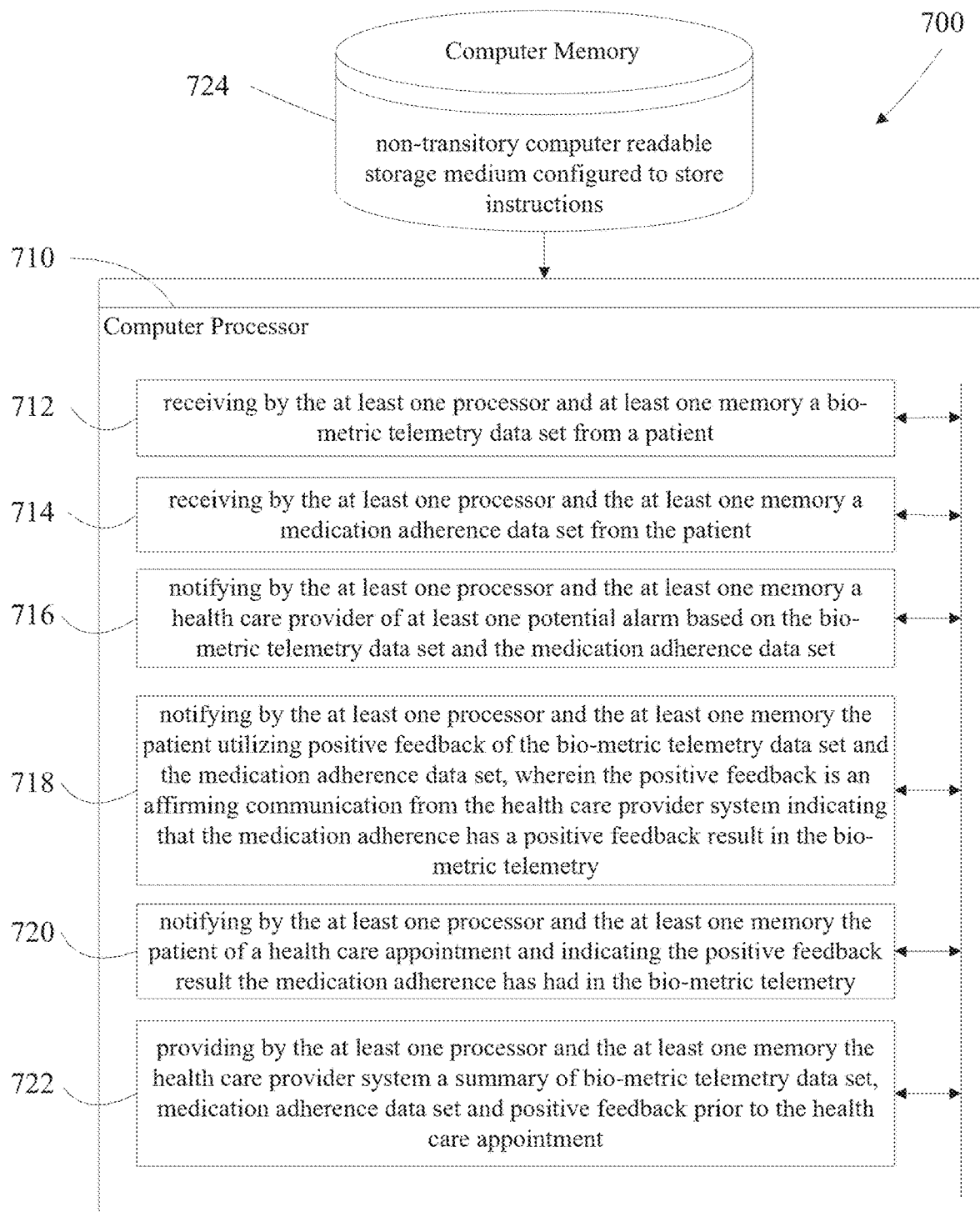
FIG. 7 depicts an example non-transitory computer readable medium in accordance with one embodiment of the disclosure.

FIG. 7 depicts a non-transitory computer readable storage medium 724 to store instructions, that when executed cause at least one computer processor 710 to perform, receiving 712 by the at least one processor and at least one memory a bio-metric telemetry data set from a patient, receiving 714 by the at least one processor and the at least one memory a medication adherence data set from the patient and notifying 716 by the at least one processor and the at least one memory a health care provider system of at least one potential alarm based on the bio-metric telemetry data set and the medication adherence data set. The non-transitory computer storage medium also notifying 718 by the at least one processor and the at least one memory the patient utilizing positive feedback of the bio-metric telemetry data set and the medication adherence data set, wherein the positive feedback is an affirming communication from the health care provider system indicating that the medication adherence has a positive feedback result in the bio-metric telemetry, notifying 720 by the at least one processor and the at least one memory the patient of a health care appointment and indicating the positive feedback result the medication adherence has had in the bio-metric telemetry and providing 722 by the at least one processor and the at least one memory the health care provider system a summary of bio-metric telemetry data set, medication adherence data set and positive feedback prior to the health care appointment.

The non-transitory computer readable storage medium may comprise receiving by the at least one processor and the at least one memory by the health care provider system at least one of at least one lab appointment data for the patient and at least one office appointment data for the patient, journaling by the at least one processor and the at least one memory the bio-metric telemetry data set, notifying by the at least one processor and the at least one memory the patient of at least one of at least an immunization, a screening and a wellness visit and notifying by the at least one processor and the at least one memory the health care provider system as to a status of the patient based on the bio-metric telemetry data set and the medication adherence data set.

Figure 18:
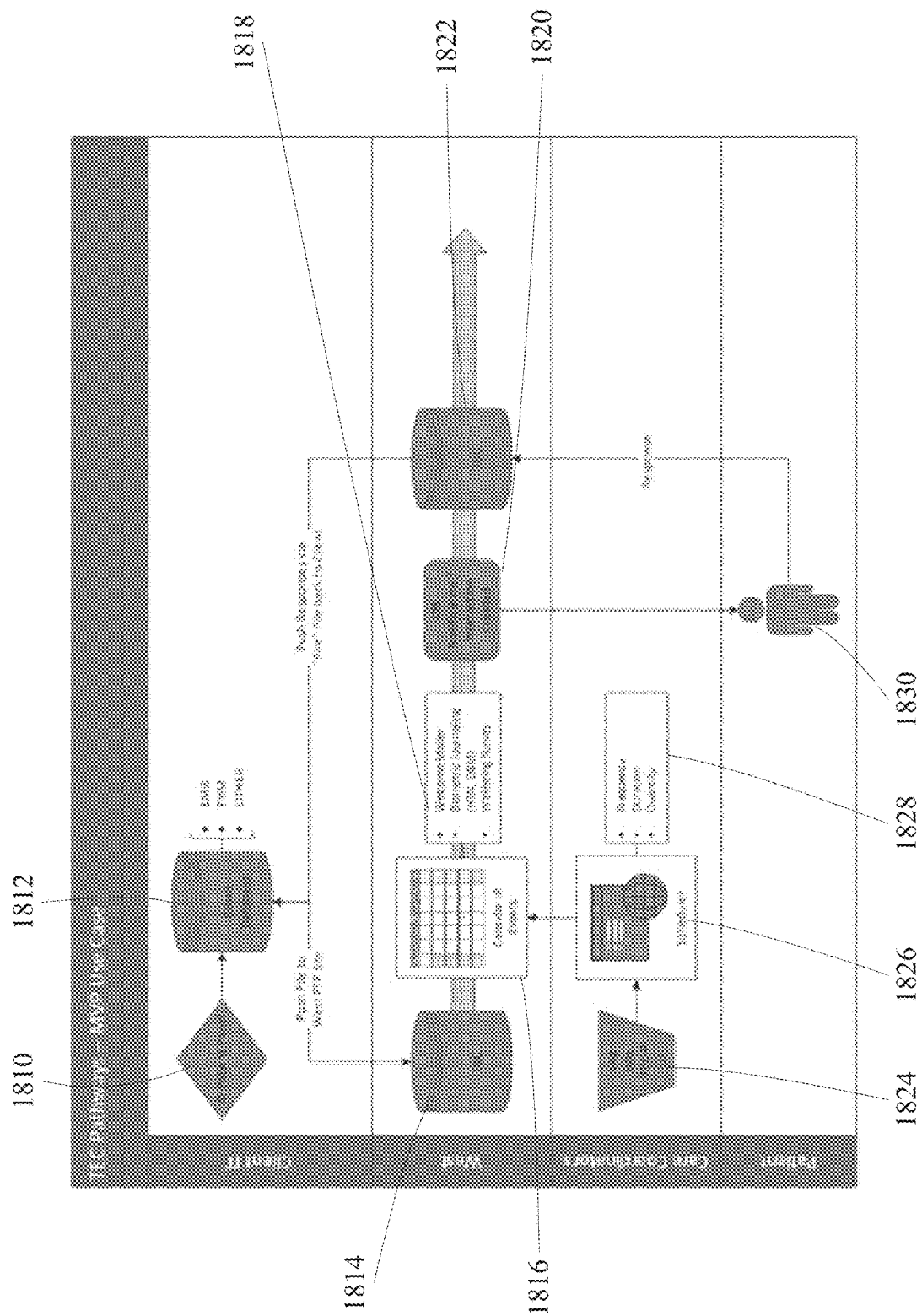
FIG. 18 depicts an example high level flow.

FIG. 18 depicts an example technology enabled communications pathway overview. The client information technology portion identifies 1810 a patient to be placed under its care and creates 1812 a client database, which may be cloud based, server based or the like. Within this patient database 1812 are the electronic medical records, the physician records and the like. A central repository 1814, 1822 receives the information from the client database 1812. Based on the information within the central repository a calendar of events is created 1816, which contains information pertaining to welcoming the patient, receiving biometric data and receiving wellness surveys from the patient 1818. Within the central repository, which may be cloud based, server based or the like, patient notifications and interaction files are created 1820 which will be sent to the patient 1830, patient responses are received by the central repository 1822. The care coordinators log into the system 1824, update the scheduler 1826 which includes frequency, duration and quantity of medication and medical visits 1828. The care coordinator interaction with the scheduler 1826 is then fed back to the scheduler 1826 for creation of a calendar of events.

Figure 19:
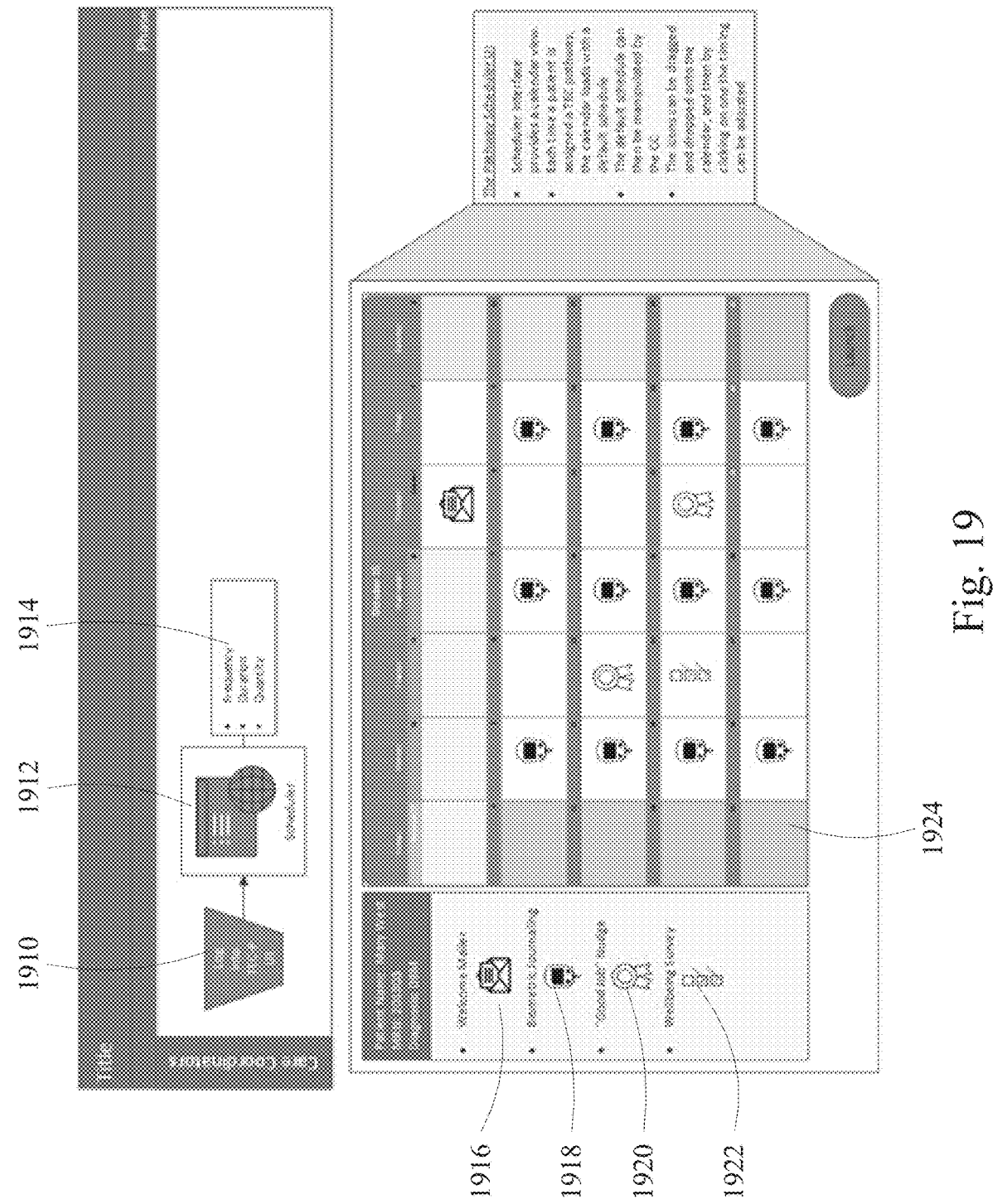
FIG. 19 depicts an example scheduler.

FIG. 19 depicts an example scheduler. The care coordinators log into the system 1910 (1824 FIG. 18), update the scheduler 1912 (1826 FIG. 18) which includes frequency, duration and quantity of medication and medical visits 1914 (1828 FIG. 18). The scheduler comprises at least a patient welcome 1916, biometric journaling 1918, data to be input for conditions of a good job nudge 1920 and when wellness surveys 1922 are to be sent to the patient. With the information received from the care coordinator a calendar 1924 is created showing the timing of each of the scheduled events.

Computer System FIG. 20 is a modification of FIG. 2 and illustrates a communication system 200 with which the current disclosure may be implemented. The conferencing system 210, has a communication fabric 212 connected to at least one processor 214 which in turn is connected to at least one memory 216 which contains instructions to control the processor and the communication fabric. In the case of a calendar mismatch FIG. 20 depicts an example calendar update and synchronization. In this example the calendar is updated 2018, utilizing the communications fabric (212 FIG. 2), processor (214 FIG. 2) and memory (216 FIG. 2) shown in FIG. 2, and resulting in a calendar synchronization 2020 on the patient side with a mobile push notification (232 FIG. 2). In this way the patient may be automatically updated for calendar changes and immediately notified.

Those skilled in the art will understand that the format, layout, and content of the data structure as shown in the figures is illustrative rather than limiting of the instant invention. Specifically, those skilled in the art will recognize that various changes, modifications, additions, omissions, or alterations may be made to the data structure shown without departing from the scope of the instant invention as recited in the claims appended hereto. More particularly, other types of computing devices such as mobile and those which provide a server function may be utilized.

The operations of a method or algorithm described in connection with the examples disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example a network element, this may represent any of the above-described network components, etc.

Although an exemplary example of at least one of the system, method, and non-transitory computer readable medium of the present disclosure has been illustrated in the accompanied drawings and described in the foregoing detailed description, it may be understood that the application is not limited to the examples disclosed, and is capable of numerous rearrangements, modifications, and substitutions without departing from the spirit or scope of the disclosure as set forth and defined by the following claims. For example, the capabilities of the systems can be performed by one or more of the modules or components described herein or in a distributed architecture.

The above examples are for illustrative purposes and are not intended to limit the scope of the disclosure or the adaptation of the features described herein to particular components. Those skilled in the art will also appreciate that various adaptations and modifications of the above-described preferred examples can be configured without departing from the scope and spirit of the disclosure. Therefore, it is to be understood that, within the scope of the appended claims, the disclosure may be practiced by examples in addition to those specifically described.

What is claimed is:

1. A method, comprising:
   storing a plurality of condition-specific libraries that each comprises a predefined sequence of communication interventions for a different patient condition;
   assigning a condition-specific library from among the plurality of condition-specific libraries to a patient based on a request from a health care provider system;
   receiving, by at least one processor, a bio-metric telemetry data set from the patient;
   receiving, by the at least one processor, a medication adherence data set and survey data from the patient;
   determining which communication interventions of the assigned condition-specific library are most pertinent to the patient based on the bio-metric telemetry data set and the medication adherence data set;
   notifying, by the at least one processor, the patient of a health care appointment based on the determined communication interventions of the assigned condition-specific library;
   providing, by the at least one processor, the health care provider system a summary of the bio-metric telemetry data and the medication adherence data set prior to the health care appointment;
   receiving, by the at least one processor, a feedback notification from the health care provider system indicating that medication inherence is having a positive impact on the bio-metric telemetry data set; and
   providing, by the at least one processor, the feedback notification from the health care provider system to a device of the patient based on preferences set by the patient.

2. The method of claim 1, further comprising:
   receiving, by the at least one processor, at least one of at least one lab appointment data for the patient and at least one office appointment data for the patient.

3. The method of claim 1, further comprising:
   journaling, by the at least one processor, the bio-metric telemetry data set.

4. The method of claim 1, further comprising:
   notifying, by the at least one processor, the patient of at least one of at least an immunization, a screening, and a wellness visit.

5. The method of claim 1, further comprising:
   notifying, by the at least one processor, the health care provider system as to a status of the patient based on the bio-metric telemetry data set and the medication adherence data set.

6. The method of claim 1, wherein the notification is based on patient preference by at least one of direct mail, voice, SMS and email.

7. The method of claim 1, wherein a notification sequence, a notification duration and a notification frequency is determined by the health care provider system.

8. The method of claim 1, wherein the health care appointment comprises at least one upcoming lab appointment and wherein a lab preparation notification is sent prior to the at least one upcoming lab appointment.

9. The method of claim 1, wherein the health care appointment comprises at least one upcoming office appointment.

10. An apparatus, comprising:
    at least processor to:
    store a plurality of condition-specific libraries that each comprises a predefined sequence of communication interventions for a different patient condition;
    assign a condition-specific library from among the plurality of condition-specific libraries to a patient based on a request from a health care provider system;
    receive a bio-metric telemetry data set from the patient;
    receive a medication adherence data set from the patient;
    determine which communication interventions of the assigned condition-specific library are most pertinent to the patient based on the bio-metric telemetry data set and the medication adherence data set;
    notify the patient of a health care appointment based on the determined communication interventions of the assigned condition-specific library;
    providing the health care provider system a summary of the bio-metric telemetry data set and the medication adherence data set prior to the health care appointment;
    receive a feedback notification from the health care provider system indicating that medication inherence is having a positive impact on the bio-metric telemetry data set; and
    provide the feedback notification from the healthcare provider system to a device of the patient based on preferences set by the patient.

11. The apparatus of claim 10, wherein the processor further is to:
    receive at least one of at least one lab appointment data for the patient and at least one office appointment data for the patient.

12. The apparatus of claim 10, wherein the processor further is to:
    journal the bio-metric telemetry data set.

13. The apparatus of claim 10, wherein the processor further is to:
    notify the patient of at least one of at least an immunization, a screening, and a wellness visit.

14. The apparatus of claim 10, wherein the processor further is to:
    notify the at least one memory the health care provider system as to a status of the patient based on the bio-metric telemetry data set and the medication adherence data set.

15. The apparatus of claim 10, wherein the notification is based on patient preference by at least one of direct mail, voice, SMS and email and wherein a notification sequence, a notification duration and a notification frequency is determined by the health care provider system.

16. A non-transitory computer readable storage medium to store instructions that when executed by at least one processor cause the at least one processor to perform:
    storing a plurality of condition-specific libraries that each comprises a predefined sequence of communication interventions for a different patient condition;
    assigning a condition-specific library from among the plurality of condition-specific libraries to a patient based on a request from a health care provider system;
    receiving, by at least one processor, a bio-metric telemetry data set from the patient;
    receiving, by the at least one processor, a medication adherence data set from the patient;
    determining which communication interventions of the assigned condition-specific library are most pertinent to the patient based on the bio-metric telemetry data set and the medication adherence data set;

notifying, by the at least one processor, the patient of a health care appointment based on the determined communication interventions of the assigned condition-specific library;

providing, by the at least one processor, the health care provider system a summary of the bio-metric telemetry data and the medication adherence data set prior to the health care appointment;

receiving, by the at least one processor, a feedback notification from the health care provider system indicating that medication inherence is having a positive impact on the bio-metric telemetry data set; and providing, by the at least one processor, the feedback notification from the health care provider system to a device of the patient based on preferences set by the patient.

17. The non-transitory computer readable storage medium of claim 16, further to store instructions that when executed by the processor causes the processor to perform:

receiving at least one of at least one lab appointment data for the patient and at least one office appointment data for the patient.

18. The non-transitory computer readable storage medium of claim 16, further to store instructions that when executed by the processor causes the processor to perform:

journaling the bio-metric telemetry data set.

19. The non-transitory computer readable storage medium of claim 16, further to store instructions that when executed by the processor causes the processor to perform:

notifying the patient of at least one of at least an immunization, a screening, and a wellness visit.

20. The non-transitory computer readable storage medium of claim 16, further to store instructions that when executed by the processor causes the processor to perform:

notifying the health care provider system as to a status of the patient based on the bio-metric telemetry data set and the medication adherence data set.

* * * * *